US012745983B2

(12) United States Patent
Sang et al.

(10) Patent No.: US 12,745,983 B2
(45) Date of Patent: Sep. 29, 2026

(54) ULTRASONIC CONTRAST IMAGING METHOD AND ULTRASONIC IMAGING APPARATUS

(71) Applicant: SHENZHEN MINDRAY BIO-MEDICAL ELECTRONICS CO., LTD., Shenzhen (CN)

(72) Inventors: Maodong Sang, Shenzhen (CN); Yuchao Sang, Shenzhen (CN); Yuan Wang, Shenzhen (CN); Zebing Wang, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 19/031,395

(22) Filed: Jan. 18, 2025

(65) Prior Publication Data

US 2025/0241621 A1 Jul. 31, 2025

(30) Foreign Application Priority Data

Jan. 26, 2024 (CN) ......................... 202410119879.5

(51) Int. Cl.
*A61B 8/00* (2006.01)
*A61B 8/08* (2006.01)

(52) U.S. Cl.
CPC ............ *A61B 8/481* (2013.01); *A61B 8/0891* (2013.01); *A61B 8/461* (2013.01); *A61B 8/5207* (2013.01)

(58) Field of Classification Search
CPC ....... A61B 8/481; A61B 8/0891; A61B 8/461; A61B 8/5207
See application file for complete search history.

(56) References Cited

U.S. PATENT DOCUMENTS

| | | | | |
|---|---|---|---|---|
| 12,160,682 | B2 * | 12/2024 | Sang | A61B 8/461 |
| 2008/0051660 | A1 * | 2/2008 | Kakadaris | A61B 8/488 600/454 |
| 2009/0054775 | A1 * | 2/2009 | Kato | G01S 7/52046 600/443 |
| 2019/0015075 | A1 * | 1/2019 | Yoshiara | A61B 8/06 |
| 2021/0014427 | A1 * | 1/2021 | Honjo | H04N 23/695 |
| 2021/0015463 | A1 * | 1/2021 | Shiran | A61B 8/0883 |
| 2021/0128093 | A1 * | 5/2021 | Vaz | A61B 6/481 |
| 2023/0127820 | A1 * | 4/2023 | Sang | A61B 8/481 386/353 |
| 2024/0358353 | A1 * | 10/2024 | Sheeran | A61B 8/469 |

* cited by examiner

*Primary Examiner* — Baisakhi Roy
(74) *Attorney, Agent, or Firm* — PV IP PC; Wei Te Chung

(57) ABSTRACT

Disclosed are ultrasonic contrast imaging methods and apparatus. Under a variable frame rate imaging mode, when a contrast agent is injected to a target object, the apparatus obtains ultrasonic data with a first imaging frame rate according to corresponding imaging parameters; when a predefined condition is met after the injection, it obtains ultrasonic data with another imaging frame rate other than the first imaging frame rate according to preconfigured imaging parameters associated with the predefined condition; and generates a contrast image having at least these two imaging frame rates based on the aforementioned two kinds of obtained ultrasonic data. Accordingly, contrast images can be generated by using different imaging frame rates during ultrasonic contrast imaging process, meeting lesion-observation requirements under different contrast phases.

12 Claims, 7 Drawing Sheets

FIG.5
INFO
PROBE
SCAN
BROWSE
REPORT
END
TISSUES
CONTRAST
FILM
Contrast
Timer 1
Timer 2
Backward Storage
Forward Storage
Dual Real-Time
Variable Frame Rate Imaging
Contrast Destruction
Extended Imaging
Off
Contrast Enhancement
Smooth
Duration
A/M
Arrival Time
t0
End Time
t1
Standard FR
FR0
High FR
FR1
Threshold
Th

ULTRASONIC CONTRAST IMAGING METHOD AND ULTRASONIC IMAGING APPARATUS

TECHNICAL FIELD

The present disclosure relates to ultrasonic imaging, in particular to ultrasonic contrast imaging methods and ultrasonic imaging apparatus.

BACKGROUND

Ultrasonic contrast imaging is an imaging method that utilizes the nonlinear vibration characteristics of microbubbles under specific acoustic field conditions to distinguish and extract nonlinear signals generated by microbubbles from linear signals generated by tissues in ultrasonic echo signals through techniques such as pulse inversion and amplitude modulation, thereby obtaining contrast ultrasonic contrast images with high sensitivity and high contrast. Ultrasonic contrast imaging, compared to conventional ultrasonic imaging, offers a clear visualization of blood perfusion within vessels and tissues. It enhances image contrast resolution, allowing for a more accurate distinction between lesions and normal tissues, and significantly boosts the sensitivity and specificity of ultrasonic diagnosis.

Extensive clinical research data demonstrates that ultrasonic contrast imaging markedly enhances the detection rate of liver diseases when compared to traditional ultrasound methods. The results obtained from this technique are highly valuable for differentiating between benign and malignant lesions. Furthermore, ultrasonic contrast imaging plays a pivotal role in tumor location and the assessment of post-operative efficacy during liver interventional therapies. To accurately distinguish hemodynamic differences between normal tissues and malignant lesions, a specific imaging frame rate is required for ultrasonic contrast imaging. Moreover, in order to minimize the disruption of microbubbles and maximize the duration of imaging, the frame rate of commonly used ultrasonic imaging equipment is typically set between 10 and 15 frames per second (fps), and the frame rate remains constant throughout each imaging session.

However, the current ultrasonic imaging equipment can only maintain a fixed imaging frame rate (e.g., 10 fps to 15 fps). When diagnosing certain diseases (such as small hypervascular lesions), using such a fixed imaging frame rate may make it difficult to obtain more accurate or satisfactory contrast images, thus increasing the difficulty of diagnosing the diseases to a certain extent.

SUMMARY

The present disclosure introduces ultrasonic contrast imaging methods and ultrasonic imaging apparatus that utilize varying imaging frame rates during the ultrasonic contrast imaging to address the requirements for observing lesions in various imaging phases.

In accordance with a first aspect of the present disclosure, some embodiments provide an ultrasonic contrast imaging method that may comprise:

in response to an instruction to enter a fixed frame rate imaging mode, entering the fixed frame rate imaging mode that is preconfigured with a fixed imaging frame rate that is preconfigured with corresponding imaging parameters; and under the fixed frame rate imaging mode: when a contrast agent is injected into a target object, according to the imaging parameters preconfigured for the fixed imaging frame rate, emitting ultrasonic waves to a region of interest of the target object and receiving ultrasonic echoes from the target object to obtain ultrasonic data with the fixed imaging frame rate, and generating a contrast image based on the ultrasonic data with the fixed imaging frame rate; and in response to an instruction to enter a variable frame rate imaging mode, entering the variable frame rate imaging mode that is preconfigured at least with a first imaging frame rate and a second imaging frame rate that are each preconfigured with corresponding imaging parameters, with the second imaging frame rate being higher than the first imaging frame rate; and under the variable frame rate imaging mode: when the contrast agent is injected into the target object, according to the imaging parameters preconfigured for the first imaging frame rate, emitting ultrasonic waves to the region of interest of the target object and receiving ultrasonic echoes from the target object to obtain ultrasonic data with the first imaging frame rate; after the contrast agent is injected and a first predefined condition is met, according to the imaging parameters preconfigured for the second imaging frame rate, emitting ultrasonic waves to the region of interest of the target object and receiving ultrasonic echoes from the target object to obtain ultrasonic data with the second imaging frame rate; and generating a contrast image based on the ultrasonic data with the first imaging frame rate and the ultrasonic data with the second imaging frame rate, wherein said contrast image has at least the first imaging frame rate and the second imaging frame rate.

In accordance with a second aspect of the present disclosure, some embodiments provide an ultrasonic contrast imaging method that may comprise:

in response to an instruction to enter a variable frame rate imaging mode, entering the variable frame rate imaging mode that is preconfigured at least with a first imaging frame rate and a second imaging frame rate that are each preconfigured with corresponding imaging parameters, with the second imaging frame rate being higher than the first imaging frame rate; and under the variable frame rate imaging mode:

when a contrast agent is injected into a target object, according to the imaging parameters preconfigured for the first imaging frame rate, emitting ultrasonic waves to a region of interest of the target object and receiving ultrasonic echoes from the target object to obtain ultrasonic data with the first imaging frame rate;

after the contrast agent is injected and a first predefined condition is met, according to the imaging parameters preconfigured for the second imaging frame rate, emitting ultrasonic waves to the region of interest of the target object and receiving ultrasonic echoes from the target object to obtain ultrasonic data with the second imaging frame rate; and generating a contrast image based on the ultrasonic data with the first imaging frame rate and the ultrasonic data with the second imaging frame rate, wherein the contrast image has at least the first imaging frame rate and the second imaging frame rate.

In an embodiment, the fixed imaging frame rate is equal to the first imaging frame rate.

In an embodiment, the first predefined condition comprises: a time period corresponding to an early arterial phase during an imaging process of the contrast agent.

In an embodiment, the time period corresponding to the early arterial phase includes a first time and a second time, wherein the first time is a start time of the early arterial phase, measured from start of the injection of the contrast agent, and the second time is an end time of the early arterial phase, measured from start of the injection of the contrast agent; and the method further comprises: obtaining the first time and/or the second time in response to a time parameter preconfigured by a user; or, automatically detecting the first time and/or the second time based on the ultrasonic data obtained according to the imaging parameters preconfigured for the first imaging frame rate.

In an embodiment, automatically detecting the first time based on the ultrasonic data obtained according to the imaging parameters preconfigured for the first imaging frame rate, comprises:

within a period of time after the contrast agent is injected, obtaining reference ultrasonic data based on the ultrasonic data obtained according to the imaging parameters preconfigured for the first imaging frame rate within said period of time;

after obtaining the reference ultrasonic data, either obtaining current ultrasonic data once every fixed time interval according to the imaging parameters preconfigured for the first imaging frame rate, and taking each obtained current ultrasonic data as target ultrasonic data or taking each frame of ultrasonic data obtained according to the imaging parameters preconfigured for the first imaging frame rate as target ultrasonic data; and determining a time when an average intensity difference between currently obtained target ultrasonic data and the reference ultrasonic data is greater than or equal to a threshold as the first time.

In an embodiment, under the variable frame rate imaging mode, the method further comprises: in response to an instruction to adjust imaging frame rate from a user, adjusting the first imaging frame rate and/or the second imaging frame rate.

In accordance with a third aspect of the present disclosure, some embodiments provide an ultrasonic contrast imaging method that may comprise:

in response to an instruction to enter a variable frame rate imaging mode, entering the variable frame rate imaging mode that is preconfigured with at least two imaging frame rates that at least include a first imaging frame rate, wherein each imaging frame rate is preconfigured with corresponding imaging parameters; and under the variable frame rate imaging mode:

within a period of time after a contrast agent is injected, according to the imaging parameters preconfigured for the first imaging frame rate, emitting ultrasonic waves to a region of interest of a target object and receiving ultrasonic echoes from the target object, so as to obtain ultrasonic data with the first imaging frame rate;

after the contrast agent is injected and a predefined condition is met, according to imaging parameters preconfigured for an imaging frame rate corresponding to the predefined condition, emitting ultrasonic waves to the region of interest of the target object and receiving ultrasonic echoes from the target object, so as to obtain ultrasonic data with the corresponding imaging frame rate, wherein each imaging frame rate corresponds to one or more predefined conditions; and generating a contrast image having at least two imaging frame rates based on the ultrasonic data with the first imaging frame rate and the ultrasonic data with at least one preconfigured imaging frame rate other than the first imaging frame rate.

In an embodiment, the predefined condition includes time periods corresponding respectively to one or more phases during an imaging process of the contrast agent.

In an embodiment, the time periods corresponding to each of the phases during the imaging process of the contrast agent include a start time and an end time of each corresponding phase, wherein the start time is a start time of each corresponding phase, measured from start of the injection of the contrast agent, and the end time is an end time of each corresponding phase, measured from start of the injection of the contrast agent; and the method further comprises: obtaining the start time and/or the end time of each corresponding phase in response to a time parameter preconfigured by a user; or, automatically detecting the start time and/or the end time of each corresponding phase based on the ultrasonic data obtained according to the imaging parameters preconfigured for the first imaging frame rate.

In an embodiment, under the variable frame rate imaging mode, the method further comprises: in response to an instruction to adjust imaging frame rate from a user, adjusting one or more of the at least two imaging frame rates.

In accordance with a fourth aspect of the present disclosure, some embodiments provide an ultrasonic imaging apparatus that may comprise:

a probe;

a transmit circuit configured to excite the probe to emit ultrasonic waves to a target object;

a receive circuit configured to receive ultrasonic echoes from the target object through the probe to obtain ultrasonic echo signals;

a processor configured to process the ultrasonic echo signals to obtain an ultrasonic image of the target object; and a display configured to display the ultrasonic image;

wherein the processor is further configured for:

in response to an instruction to enter a fixed frame rate imaging mode, entering the fixed frame rate imaging mode that is preconfigured with a fixed imaging frame rate that is preconfigured with corresponding imaging parameters; and under the fixed frame rate imaging mode: when a contrast agent is injected into a target object, according to the imaging parameters preconfigured for the fixed imaging frame rate, emitting ultrasonic waves to a region of interest of the target object and receiving ultrasonic echoes from the target object to obtain ultrasonic data with the fixed imaging frame rate, and generating a contrast image based on the ultrasonic data with the fixed imaging frame rate; and in response to an instruction to enter a variable frame rate imaging mode, entering a variable frame rate imaging mode that is preconfigured at least with a first imaging frame rate and a second imaging frame rate that are each preconfigured with corresponding imaging parameters, with the second imaging frame rate being greater than the first imaging frame rate; and under the variable frame rate imaging mode: when the contrast agent is injected into a target object, according to the imaging parameters preconfigured for the first imaging frame rate, emitting ultrasonic waves to a region of interest of the target object and receiving ultrasonic echoes from the target object to obtain ultrasonic data with the first imaging frame rate; after the contrast agent is injected and a first predefined condition is met, according to the imaging parameters preconfigured for the second imaging frame rate, emitting ultrasonic waves to the region of interest of the target object and receiving ultrasonic echoes from the target object to obtain ultrasonic data with the second imaging frame rate; and generating a contrast image based on the ultrasonic data with the first imaging frame rate and the ultrasonic data with the second imaging frame rate, wherein the contrast image has at least the first imaging frame rate and the second imaging frame rate.

In accordance with a fifth aspect of the present disclosure, some embodiments provide an ultrasonic imaging apparatus that may comprise:

a probe;

a transmit circuit configured to excite the probe to emit ultrasonic waves to a target object;

a receive circuit configured to receive ultrasonic echoes from the target object through the probe to obtain ultrasonic echo signals;

a processor configured to process the ultrasonic echo signals to obtain an ultrasonic image of the target object; and a display configured to display the ultrasonic image;

wherein the processor is further configured for:

in response to an instruction to enter a variable frame rate imaging mode, entering the variable frame rate imaging mode that is preconfigured at least with a first imaging frame rate and a second imaging frame rate that are each preconfigured with corresponding imaging parameters, with the second imaging frame rate being greater than the first imaging frame rate; and under the variable frame rate imaging mode:

when a contrast agent is injected into a target object, according to the imaging parameters preconfigured for the first imaging frame rate, emitting ultrasonic waves to a region of interest of the target object and receiving ultrasonic echoes from the target object to obtain ultrasonic data with the first imaging frame rate;

after the contrast agent is injected and a first predefined condition is met, according to the imaging parameters preconfigured for the second imaging frame rate, emitting ultrasonic waves to the region of interest of the target object and receiving ultrasonic echoes from the target object to obtain ultrasonic data with the second imaging frame rate; and generating a contrast image based on the ultrasonic data with the first imaging frame rate and the ultrasonic data with the second imaging frame rate, wherein the contrast image has at least the first imaging frame rate and the second imaging frame rate.

In an embodiment, the fixed imaging frame rate is equal to the first imaging frame rate.

In an embodiment, the first predefined condition comprises: a time period corresponding to an early arterial phase during an imaging process of the contrast agent.

In an embodiment, the time period corresponding to an early arterial phase includes a first time and a second time, wherein the first time is a start time of the early arterial phase, measured from start of the injection of the contrast agent, and the second time is an end time of the early arterial phase, measured from start of the injection of the contrast agent; and the processor is further configured for: obtaining the first time and/or the second time in response to a time parameter preconfigured by a user; or, automatically detecting the first time and/or the second time based on the ultrasonic data obtained according to the imaging parameters preconfigured for the first imaging frame rate.

In an embodiment, automatically detecting the first time based on the ultrasonic data obtained according to the imaging parameters preconfigured for the first imaging frame rate comprises: within a period of time after the contrast agent is injected, obtaining reference ultrasonic data based on the ultrasonic data obtained according to the imaging parameters preconfigured for the first imaging frame rate; after obtaining the reference ultrasonic data, either obtaining current ultrasonic data once every fixed time interval according to the imaging parameters preconfigured for the first imaging frame rate and taking each obtained current ultrasonic data as target ultrasonic data, or taking each frame of ultrasonic data obtained according to the imaging parameters preconfigured for the first imaging frame rate as target ultrasonic data; and determining a time when an average intensity difference between currently obtained target ultrasonic data and the reference ultrasonic data is greater than or equal to a threshold as the first time.

In an embodiment, the processor is further configured for: under the variable frame rate imaging mode, in response to an instruction to adjust imaging frame rate from a user, adjusting the first imaging frame rate and/or the second imaging frame rate.

In accordance with a sixth aspect of the present disclosure, some embodiments provide an ultrasonic imaging apparatus that may comprise:

a probe;

a transmit circuit configured to excite the probe to emit ultrasonic waves to a target object;

a receive circuit configured to receive ultrasonic echoes from the target object through the probe to obtain ultrasonic echo signals;

a processor configured to process the ultrasonic echo signals to obtain an ultrasonic image of the target object; and a display configured to display the ultrasonic image;

wherein the processor is further configured for:

in response to an instruction to enter a variable frame rate imaging mode, entering the variable frame rate imaging mode that is preconfigured with at least two imaging frame rates that at least include a first imaging frame rate, wherein each imaging frame rate is preconfigured with corresponding imaging parameters; and under the variable frame rate imaging mode:

within a period of time after the contrast agent is injected, according to the imaging parameters preconfigured for the first imaging frame rate, emitting ultrasonic waves to a region of interest of the target object and receiving ultrasonic echoes from the target object so as to obtain ultrasonic data with the first imaging frame rate;

after the contrast agent is injected and a predefined condition is met, according to imaging parameters preconfigured for an imaging frame rate corresponding to the predefined condition, emitting ultrasonic waves to the region of interest of the target object and receiving ultrasonic echoes from the target object so as to obtain ultrasonic data with the corresponding imaging frame rate, wherein each imaging frame rate corresponds to one or more predefined conditions; and generating a contrast image having at least two imaging frame rates based on the ultrasonic data with the first imaging frame rate and ultrasonic data with at least one preconfigured imaging frame rate other than the first imaging frame rate.

In an embodiment, the predefined condition includes time periods corresponding respectively to one or more phases during an imaging process of the contrast agent.

In an embodiment, the time periods corresponding to each of the phases during the imaging process of the contrast agent include a start time and an end time of each corresponding phase, wherein the start time is a start time of each corresponding phase, measured from start of the injection of the contrast agent, and the end time is an end time of each corresponding phase, measured from start of the injection of the contrast agent; and the processor is further configured for: obtaining the start time and/or the end time of each corresponding phase in response to a time parameter preconfigured by a user; or, automatically detecting the start time and/or the end time of each corresponding phase based on the ultrasonic data obtained according to the imaging parameters preconfigured for the first imaging frame rate.

In an embodiment, the processor is further configured for: under the variable frame rate imaging mode, in response to an instruction to adjust imaging frame rate from a user, adjusting one or more of the at least two imaging frame rates.

In accordance with a seventh aspect of the present disclosure, some embodiments provide a computer-readable storage medium, on which a program is stored, wherein the program is executed by a processor to implement the method described in any one of the aforementioned embodiments.

According to the ultrasonic contrast imaging methods and the ultrasonic imaging apparatus in the aforementioned embodiments, under the variable frame rate imaging mode, when the contrast agent is injected into the target object, the ultrasonic imaging apparatus can obtain ultrasonic data with the first imaging frame rate according to the imaging parameters corresponding to the first imaging frame rate, and after the contrast agent is injected and a predefined condition is met, the ultrasonic imaging apparatus can obtain ultrasonic data with the corresponding imaging frame rate according to the imaging parameters preconfigured for an imaging frame rate corresponding to the predefined condition, and, based on the ultrasonic data with the first imaging frame rate and the ultrasonic data with at least one preconfigured imaging frame rate other than the first imaging frame rate, generate a contrast image having at least two imaging frame rate. Through the above approach, different imaging frame rates can be used to generate contrast images during the ultrasonic contrast-enhanced imaging process, meeting the observation requirements for lesions under different imaging phases.

DETAILED DESCRIPTION

Figure 1:
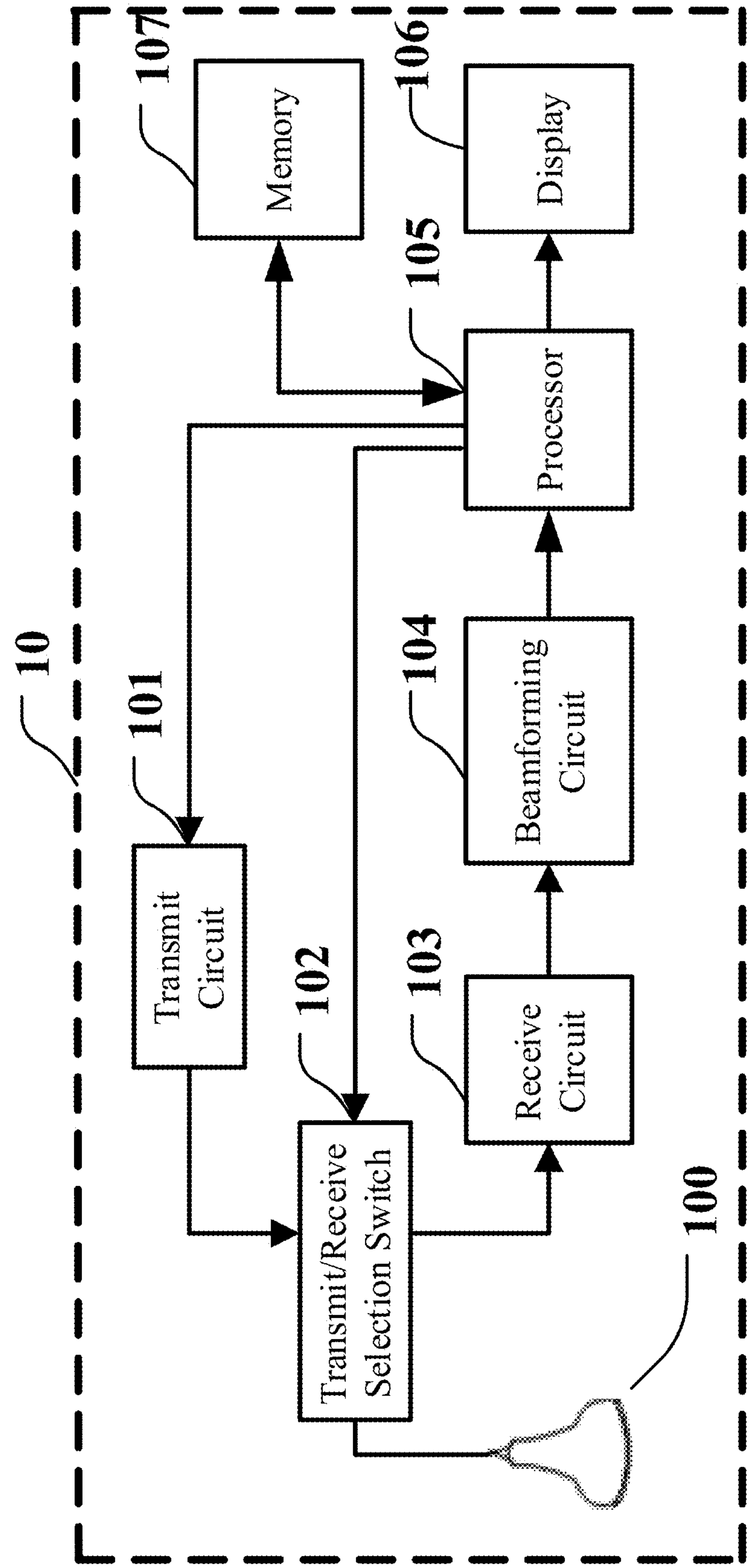
FIG. 1 is a schematic structural diagram of an ultrasonic imaging apparatus according to some embodiments.

The present disclosure will be further described in detail below through specific embodiments with reference to the accompanying drawings. Common or similar elements are referenced with like or identical reference numerals in different embodiments. Many details described in the following embodiments are for better understanding the present disclosure. However, those skilled in the art can realize with minimal effort that some of these features can be omitted in different cases or be replaced by other elements, materials and methods. For clarity some operations related to the present disclosure are not shown or illustrated herein so as to prevent the core from being overwhelmed by excessive descriptions. For those skilled in the art, such operations are not necessary to be explained in detail, and they can fully understand the related operations according to the description in the specification and the general technical knowledge in the art.

In addition, the features, operations or characteristics described in the specification may be combined in any suitable manner to form various embodiments. At the same time, the steps or actions in the described method can also be sequentially changed or adjusted in a manner that can be apparent to those skilled in the art. Therefore, the various sequences in the specification and the drawings are only for the purpose of describing a particular embodiment, and are not intended to be an order of necessity, unless otherwise stated one of the sequences must be followed.

The serial numbers of components herein, such as “first”, “second”, etc., are only used to distinguish the described objects and do not have any order or technical meaning. The terms “connected”, “coupled” and the like here include direct and indirect connections (coupling) unless otherwise specified.

Taking liver contrast imaging as an example, the phases of ultrasonic contrast imaging are explained below.

A contrast agent enters the liver through two pathways, namely the celiac artery-hepatic artery and the portal vein-hepatic sinusoids. During real-time contrast imaging, three typical vascular phases can be observed (if Sonazoid contrast agent is used, an additional phase called the “Kupffer phase” is observed):

1. Arterial phase: It starts 10-20 seconds after the injection of the contrast agent and ends 30-45 seconds later. During the arterial phase, arterial vessels within the liver parenchyma become visible and rapidly enhanced, with clear visualization of the perfusion process of the vascular branches. The echo of the liver parenchyma also gradually increases as the contrast agent enters the microvessels and hepatic sinusoids. The contrast-enhanced findings in the early arterial phase are crucial for the differential diagnosis of tumors, particularly in distinguishing malignant liver tumors.

2. Portal venous phase: It starts 30-45 seconds after the injection of the contrast agent and ends 120 seconds later. In the portal venous phase, the portal vein and its main branches in the liver are filled with the contrast agent, reaching a peak signal intensity that gradually decreases after maintaining for a period of time.

3. Delayed phase: It starts 120 seconds after the injection of the contrast agent and continues until the microbubbles rupture (disappear). The contrast signal in the liver vessels and tissues gradually decreases to a level before the injection of the contrast agent.

In summary, based on the characteristic contrast performances of different liver diseases observed in various phases, the results can serve as an important auxiliary tool and provide a diagnostic basis for clinically differentiating between different diseases.

In liver contrast imaging, some small lesions with rich blood supply exhibit very rapid perfusion in the early arterial phase, making it often difficult to clearly visualize the perfusion process and vascular morphology of such lesions at standard frame rates (10 fps). Therefore, compared to other phases, the arterial phase or the early arterial phase requires an increased frame rate to obtain higher temporal resolution, allowing for clear observation of the perfusion details of small lesions. In contrast, for the portal venous phase and the delayed phase, the focus is on observing differences in the intensity of contrast signals across different parts of the liver and the trend of their changes over time. The requirement for temporal resolution is reduced in these phases, with greater emphasis on the duration and sensitivity of the contrast signals. Although high-frame-rate contrast imaging can significantly increase the frame rate, such as to more than four times the standard frame rate, meeting the need to observe perfusion details in small lesions, maintaining a high frame rate throughout the entire process may cause greater damage to contrast microbubbles. This can lead to weakened intensity and reduced duration of contrast signals, which is not conducive to the observation of the portal venous phase and the delayed phase. Additionally, the increase in frame rate achieved by high frame rate contrast imaging technique sometimes comes at the expense of losing signal-to-noise ratio in the echoes of deep tissues, which also hinders the observation of deep lesions.

Based on the aforementioned issues, some embodiments of the present disclosure provide a variable frame rate imaging mode for an ultrasonic imaging apparatus. Under the variable frame rate imaging mode, when a contrast agent is injected into a target object, ultrasonic imaging is first performed according to imaging parameters corresponding to a first imaging frame rate to obtain ultrasonic data with the first imaging frame rate; subsequently, after the contrast agent has been injected and a predefined condition (indicating the transition into different imaging phases) is met, ultrasonic imaging is performed according to imaging parameters preconfigured for the imaging frame rate corresponding to the predefined condition (different phases) to acquire ultrasonic data with the corresponding imaging frame rate; and finally, based on the ultrasonic data with the first imaging frame rate and the ultrasonic data with at least one preconfigured imaging frame rate other than the first imaging frame rate, a contrast image with at least two imaging frame rate can be generated. In this way, different imaging frame rates can be used in different phases during the contrast imaging process to meet the observation requirements for lesions in various contrast phases.

Referring to FIG. 1, an ultrasonic imaging apparatus 10 in some embodiments may include a probe 100, a transmit circuit 101, a transmit/receive selection switch 102, a receive circuit 103, a beamforming circuit, a processor 105 and a display 106. The transmit circuit 101 can excite the probe 100 to emit ultrasonic waves to a target object. The receive circuit 103 can receive ultrasonic echoes from the target object through the probe 100, thereby obtaining ultrasonic echo signals. The ultrasonic echo signals can be processed by the beamforming circuit 104 for beamforming and then sent to the processor 105. The processor 105 can process the ultrasonic echo signals to obtain an ultrasonic image of the target object that can be stored in a memory 107, or be displayed on the display 106.

In some embodiments of the present disclosure, the display 106 of the aforementioned ultrasonic imaging apparatus 10 can be a touch screen display, an LCD screen, etc., or it can be an independent display device such as an LCD monitor, a television, etc., separate from the ultrasonic imaging apparatus 10. It can also be the display screen of electronic devices such as mobile phones, tablets, etc.

In some embodiments of the present disclosure, the memory 107 of the aforementioned ultrasonic imaging apparatus 10 can be a flash memory card, a solid-state memory, a hard disk, etc.

In some embodiments of the present disclosure, a computer-readable storage medium storing a plurality of program instructions is also provided. When these program instructions are invoked and executed by the processor 105, they can perform some or all steps or any combination of steps in the contrast imaging methods described in the aforementioned embodiments.

In some embodiments of the present disclosure, the computer-readable storage medium may be the memory 107, which can be a non-volatile storage medium such as a flash memory card, a solid-state memory, a hard disk, etc.

In some embodiments of the present disclosure, the processor 105 of the aforementioned ultrasonic imaging apparatus 10 can be implemented by software, hardware, firmware or a combination thereof. It may utilize circuits, one or more application specific integrated circuits (ASICx), one or more general-purpose integrated circuits, one or more microprocessors, one or more programmable logic devices, or combinations of the aforementioned circuits or devices, or other suitable circuits or devices, thereby enabling the processor 105 to execute the corresponding steps of the contrast imaging methods described in the aforementioned embodiments.

Figure 2:
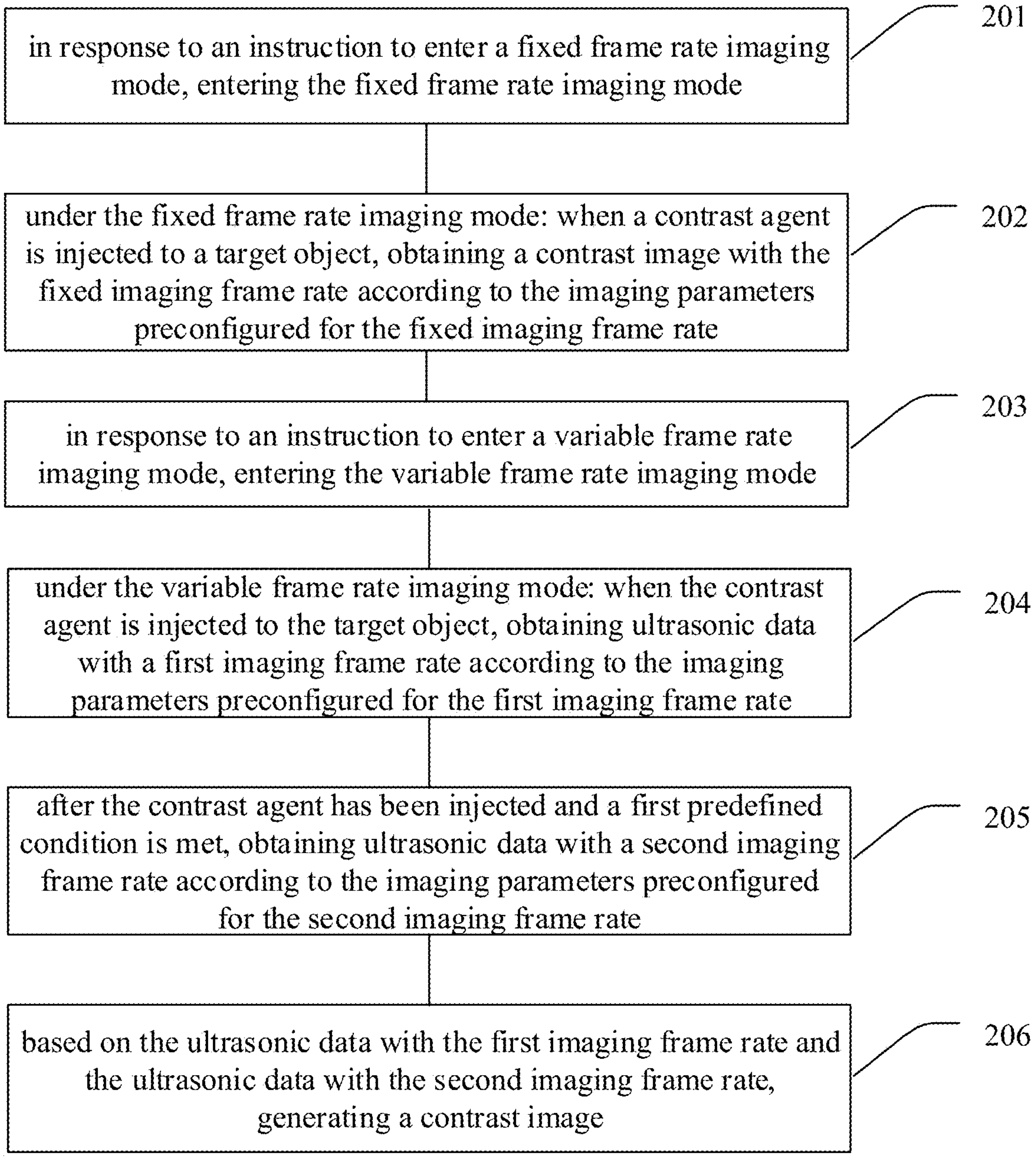
FIG. 2 is a flowchart of an ultrasonic contrast imaging method according to some embodiments.

Below is a detailed description of the ultrasonic contrast imaging method according to some embodiments. Referring to FIG. 2, the ultrasonic contrast imaging method in some embodiments can be applied to the ultrasonic imaging apparatus 10 and may include the following steps:

Step 201: in response to an instruction to enter a fixed frame rate imaging mode, entering the fixed frame rate imaging mode. The fixed frame rate imaging mode may be preconfigured with a fixed imaging frame rate, which in turn may be preconfigured with corresponding imaging parameters.

In some embodiments of the present disclosure, the instruction to enter the fixed frame rate imaging mode may be an operational instruction input by a user through a touchscreen display or an external input device, or it may be a control instruction input by the user through voice input.

Step 202: under the fixed frame rate imaging mode: when a contrast agent is injected to a target object, according to the imaging parameters preconfigured for the fixed imaging frame rate, emitting ultrasonic waves to the region of interest of the target object and receiving ultrasonic echoes from the target object to obtain ultrasonic data with the fixed imaging frame rate; and generating a contrast image based on the ultrasonic data with the fixed imaging frame rate. In the shown embodiment, the processor 105 may, according to the fixed imaging frame rate, emit ultrasonic waves to the region of interest of the target object and receive ultrasonic echoes from the target object; or, the processor 105 may emit ultrasonic waves to the target object according to the fixed imaging frame rate and receive ultrasonic echoes from the target object according to the fixed imaging frame rate; or, the processor 105 may emit ultrasonic waves to the target object, and receive ultrasonic echoes from the target object according to the fixed imaging frame rate. In all cases, ultrasonic echoes can be acquired.

It should be noted that the target object specifically refers to the physiological structure to be examined, such as the liver, heart, stomach, spleen, etc., which is not limited here.

Step 203: in response to an instruction to enter a variable frame rate imaging mode, entering the variable frame rate imaging mode. The variable frame rate imaging mode may at least be preconfigured with a first imaging frame rate and a second imaging frame rate; and the first imaging frame rate and the second imaging frame rate may each be preconfigured with corresponding imaging parameters, with the second imaging frame rate being greater than the first imaging frame rate.

In some embodiments, the ultrasonic imaging apparatus can be preset with two contrast imaging modes, namely the fixed frame rate imaging mode and the variable frame rate imaging mode, allowing users to select one as the current contrast-enhanced ultrasonic imaging mode. Under the fixed frame rate imaging mode, a single imaging frame rate (served as the fixed imaging frame rate) is used for ultrasonic imaging throughout the entire imaging process. Under the variable frame rate imaging mode, at least two different imaging frame rates can be used for ultrasonic contrast imaging during the process.

In some embodiments, the instruction to enter the variable frame rate imaging mode may be an operational instruction input by a user through a touchscreen display or an external input device, or it may be a control instruction input by the user through voice input.

In some embodiments, taking the variable frame rate imaging mode with two imaging frame rates as an example, the first imaging frame rate and the second imaging frame rate are different, with the second imaging frame rate being higher than the first imaging frame rate. For example, the first imaging frame rate ranges from 0 frames per second (fps) to 10 fps, while the second imaging frame rate ranges from 10 fps to 20 fps. Of course, in practical applications, the first imaging frame rate and the second imaging frame rate may be adjusted and are not limited to these specific ranges.

Step 204: under the variable frame rate imaging mode: when the contrast agent is injected to the target object, according to the imaging parameters preconfigured for the first imaging frame rate, emitting ultrasonic waves to the region of interest of the target object and receive ultrasonic echoes from the target object so as to obtain ultrasonic data with the first imaging frame rate. The process of emitting ultrasonic waves to the region of interest of the target object and receiving ultrasonic echoes from the target object according to the imaging parameters preconfigured for the first imaging frame rate can refer to, as described above, the specific process of emitting ultrasonic waves to the region of interest of the target object and receiving ultrasonic echoes from the target object according to the imaging parameters preconfigured for the fixed imaging frame rate.

In some embodiments, the first imaging frame rate in the variable frame rate imaging mode is equal to the fixed imaging frame rate in the fixed frame rate imaging mode.

Step 205: after the contrast agent has been injected and a first predefined condition is met, according to the imaging parameters preconfigured for the second imaging frame rate, emitting ultrasonic waves to the region of interest of the target object and receiving ultrasonic echoes from the target object so as to obtain ultrasonic data with the second imaging frame rate. The process of emitting ultrasonic waves to the region of interest of the target object and receiving ultrasonic echoes from the target object according to the imaging parameters preconfigured for the second imaging frame rate can refer to, as described above, the specific process of emitting ultrasonic waves to the region of interest of the target object and receiving ultrasonic echoes from the target object according to the imaging parameters preconfigured for the fixed imaging frame rate.

When the contrast agent starts to be injected into the target object without meeting the first predefined condition, the processor 105 may initially perform ultrasonic contrast imaging according to the first imaging frame rate (the fixed imaging frame rate); and when the processor 105 detects that the first predefined condition is met, it may perform ultrasonic contrast imaging according to the second imaging frame rate. That is, except for the period when the first predefined condition is met, during which ultrasonic imaging is performed according to the second imaging frame rate, ultrasonic imaging is performed according to the first imaging frame rate for the rest of the time.

In some embodiments, the first predefined condition may include the time period corresponding to an early arterial phase during the imaging process of the contrast agent. As known from the aforementioned liver contrast imaging process, it typically includes three phases, namely arterial phase, portal phase, and delayed phase. Since the contrast performance in the time period corresponding to an early arterial phase is crucial for the differential diagnosis of tumors, a higher imaging frame rate, i.e., the second imaging frame rate, is used for ultrasonic imaging during this corresponding time period of the arterial phase.

Figure 3:
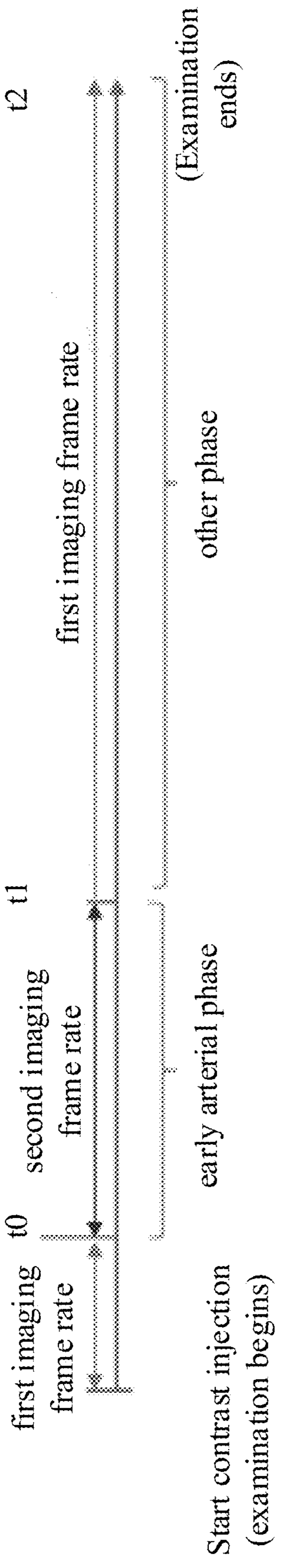
FIG. 3 is a schematic diagram illustrating the process of contrast imaging under the variable frame rate imaging mode according to some embodiments.

In some embodiments, referring to FIG. 3, the specific process of contrast imaging under the variable frame rate imaging mode may be as follows: when the contrast agent starts to be injected into the target object but the microbubbles corresponding to the contrast agent have not yet arrived, the processor 105 images using the first imaging frame rate F0 (e.g., 10 fps); and when the microbubbles corresponding to the contrast agent begin to arrive (that is, the early arterial phase begins), the processor 105 performs ultrasonic contrast imaging using the second imaging frame rate F1 (e.g., 20 fps), and after a period of time (marking the end of the early arterial phase), it automatically switches back to the first imaging frame rate F0 and continues imaging until the process is completed.

In some embodiments, the time period corresponding to an early arterial phase includes a first time and a second time. The first time is a start time of the early arterial phase, measured from start of the injection of the contrast agent; that is, the starting time of the early arterial phase, which is denoted as to in the shown embodiment. The second time is an end time of the early arterial phase, measured from start of the injection of the contrast agent; that is, the ending time of the early arterial phase, which is denoted as t1 in the shown embodiment.

Figure 4:
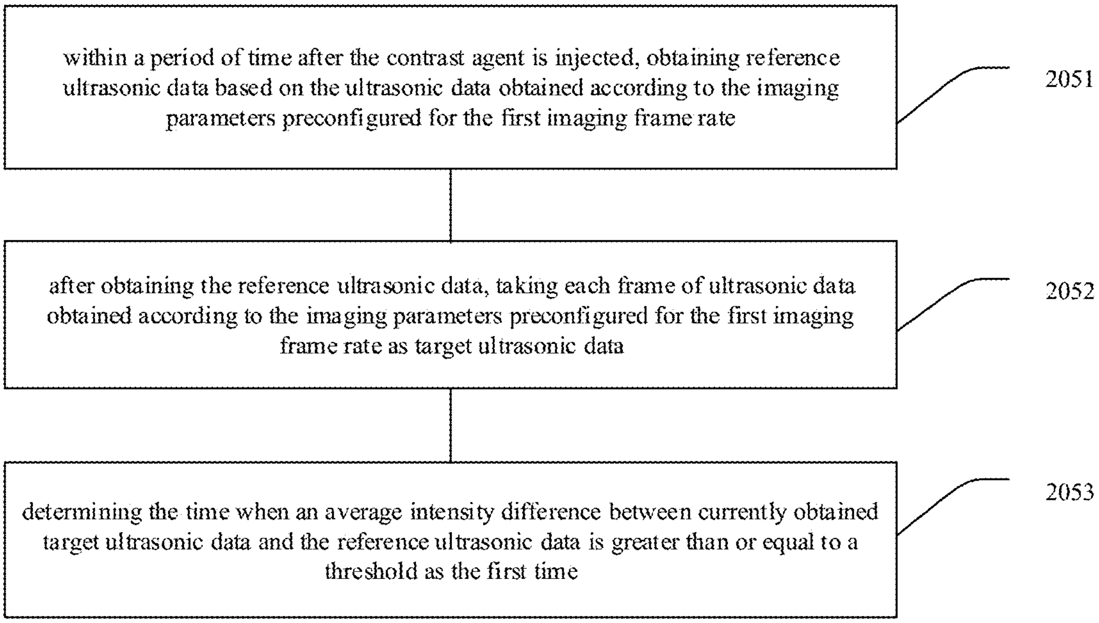
FIG. 4 is a flowchart of a method for automatically detecting the first time according to some embodiments.

The above first time and the second time can be set manually by a user or automatically set by the system. The ultrasonic imaging apparatus 10 can be preconfigured with both manual and automatic setting functions, allowing the user to select between them. When manual setting is chosen, in response to a time parameter preconfigured by the user, the first time and/or the second time can be obtained. Manual setting can be achieved through operational instructions input by the user via a touchscreen display, an external input device, or even voice control instructions; that is, the user manually inputs the first time and the second time. When automatic setting is chosen, the processor 105 can detect automatically the first time and/or the second time based on the ultrasonic data obtained according to the imaging parameters preconfigured for the first imaging frame rate In some embodiments, referring to FIG. 4, the step of automatically detecting the first time based on the ultrasonic data obtained according to the imaging parameters preconfigured for the first imaging frame rate includes the following steps:

Step 2051: within a period of time after the contrast agent is injected, the processor 105 obtaining reference ultrasonic data based on the ultrasonic data obtained according to the imaging parameters preconfigured for the first imaging frame rate;

Step 2052: after obtaining the reference ultrasonic data, the processor 105 obtaining current ultrasonic data once every fixed time interval according to the imaging parameters preconfigured for the first imaging frame rate and taking each obtained current ultrasonic data as target ultrasonic data; or, after obtaining the reference ultrasonic data, it taking each frame of ultrasonic data obtained according to the imaging parameters preconfigured for the first imaging frame rate as target ultrasonic data; and Step 2053: the processor 105 determining the time when an average intensity difference between currently obtained target ultrasonic data and the reference ultrasonic data is greater than or equal to a threshold Th as the first time.

The above is some description of the two settings for the first time and the second time corresponding to the early arterial phase.

In some embodiments, the first imaging frame rate and/or the second imaging frame rate can also be adjusted by the user within a certain range. The processor 105 can, in response to an instruction to adjust imaging frame rate from the user, adjust the first imaging frame rate and/or the second imaging frame rate.

Figure 5:
FIG. 5 is a control and display interface for ultrasonic contrast imaging according to some embodiments.

Referring to FIG. 5, a control and display interface for ultrasonic contrast imaging is illustrated. The functions implemented by the controls display on this interface may include such as: automatic/manual selection, arrival time to, ending time t1, standard frame rate (the first imaging frame rate) FR0, high frame rate (the second imaging frame rate) FR1, detection threshold Th, selection of the variable frame rate imaging mode, and so on. The following describes the manual setting of relevant parameters by the user and the automatic setting of relevant parameters under the variable frame rate imaging mode by the system, based on the control and display interface shown in the figure.

When the settings are made manually by the user: Firstly, enter the contrast-enhanced ultrasound imaging. Then, choose to enter the variable frame rate imaging mode. Next, select to set relevant parameters manually through the automatic/manual control. At this point, the controls corresponding to these relevant parameters on the display interface change from being unselectable (gray) to being changeable (white). After setting the relevant parameters, the normal contrast imaging process begins, and contrast imaging with variable frame rates can be achieved. In some embodiments, whether t0 and t1 have been reached can be determined by the processor 105 starting a preset default timer to count time. For the contrast imaging of the liver, the starting time to of the early arterial phase may be 10 s, t1 may be 20 s, the first imaging frame rate FR0 may be 10 fps, and the second imaging frame rate FR1 may be 20 fps. The user can adjust the above parameters within a certain range, for example, to can be set within 0-10 s, t1 can be set within 5 s-30 s, and FR0 and FR1 can be set within 0-10 fps and 10-20 fps, respectively. In some embodiments, the user can manually set the relevant parameters by inputting an operational instruction via a touch screen display or an external input device, or by inputting control instructions via voice input.

When the automatic setting option is selected: The parameter to does not require manual setting. Instead, the system automatically monitors the arrival time of microbubbles. For other parameters, the time periods of different phases and corresponding frame rates are still determined based on the previously built-in settings. The specific process is as follows:

Upon entering the contrast-enhanced ultrasonic imaging mode, the system initiates contrast imaging at the frame rate FR0, and simultaneously, the ultrasonic data acquired within a specific time period (ranging from 0.5 s to 1 s or the duration of a respiratory cycle) after starting the timer may be regarded as the reference data. Subsequently, either the current frame of ultrasonic data collected every fixed time interval (such as 0.5 s) is taken as target data, or each frame following the reference data without the fixed time interval is taken as the target data. An average intensity difference between the target data and the reference data is computed and compared by means of a preset algorithm. When this average intensity difference exceeds the detection threshold Th (such as 10%/15%/20%), it is considered that the contrast microbubbles have reached, and the current time is recorded as to. At the same time, the system performs contrast imaging at a high frame rate (the second imaging frame rate) during the period from t0 to t1 according to the built-in parameters FR1 and t1, while performing contrast imaging at standard frame rate (the first imaging frame rate) during the rest of the time, thus completing contrast imaging with variable frame rates.

It should be noted that once one of the manual or automatic settings is selected, it cannot be changed when the timer is on. To reset it, the timer must be stopped and then the operation can be carried out.

Step 206: based on the ultrasonic data with the first imaging frame rate and the ultrasonic data with the second imaging frame rate, generating a contrast image at least that has the first imaging frame rate and the second imaging frame rate.

The ultrasonic contrast imaging method provided by the above embodiments has two preset imaging modes, namely the fixed frame rate imaging mode and the variable frame rate imaging mode. Under the fixed frame rate imaging mode, contrast imaging can be performed at a fixed imaging frame rate throughout the entire imaging process; and under the variable frame rate imaging mode, contrast imaging can be performed at least at the first imaging frame rate and the second imaging frame rate during the contrast imaging process.

Figure 6:
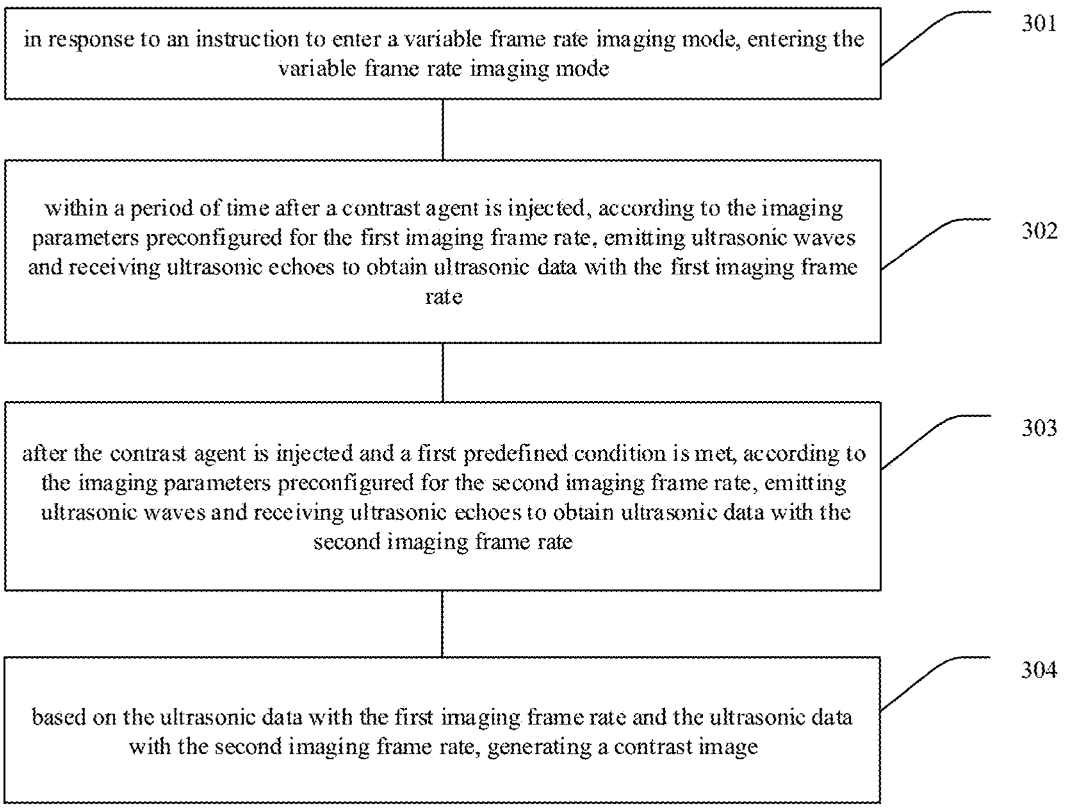
FIG. 6 is a flowchart of an ultrasonic contrast imaging method according to some other embodiments.

Referring to FIG. 6, the ultrasonic contrast imaging method in some embodiments may include the following steps:

Step 301: in response to an instruction to enter a variable frame rate imaging mode, entering the variable frame rate imaging mode. The variable frame rate imaging mode is at least preconfigured with a first imaging frame rate and a second imaging frame rate. The first imaging frame rate and the second imaging frame rate are each preconfigured with corresponding imaging parameters, with the second imaging frame rate being greater than the first imaging frame rate.

Step 302: under the variable frame rate imaging mode: within a period of time after a contrast agent is injected, according to the imaging parameters preconfigured for the first imaging frame rate, emitting ultrasonic waves to the region of interest of the target object and receiving ultrasonic echoes from the target object so as to obtain ultrasonic data with the first imaging frame rate.

Step 303: after the contrast agent is injected and a first predefined condition is met, according to the imaging parameters preconfigured for the second imaging frame rate, emitting ultrasonic waves to the region of interest of the target object and receiving ultrasonic echoes from the target object so as to obtain ultrasonic data with the second imaging frame rate.

Step 304: based on the ultrasonic data with the first imaging frame rate and the ultrasonic data with the second imaging frame rate, generating a contrast image that at least has the first imaging frame rate and the second imaging frame rate.

The specific implementation methods for the procedural steps from Step 301 to Step 304 can refer to some explanations provided in Steps 203 to 206 of the aforementioned embodiments.

Figure 7:
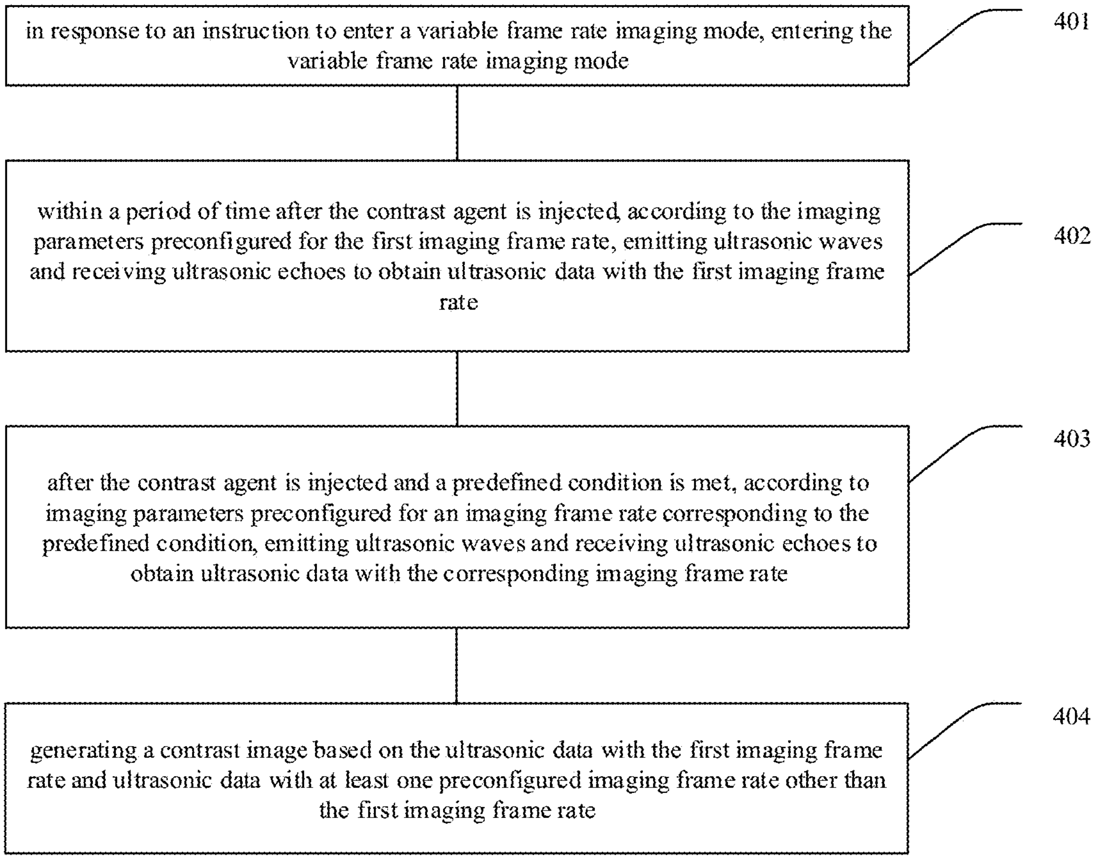
FIG. 7 a flowchart of an ultrasonic contrast imaging method according to some still other embodiments.

In the above embodiments, the contrast image obtained under the variable frame rate imaging mode at least has a first imaging frame rate and a second imaging frame rate. In this respect, referring to FIG. 7, an ultrasonic contrast imaging method is also provided in some embodiments of the present disclosure, in which the contrast image obtained under the variable frame rate imaging mode has different imaging frame rates at different phases of contrast imaging. The ultrasonic contrast imaging method may include the following steps:

Step 401: in response to an instruction to enter a variable frame rate imaging mode, entering the variable frame rate imaging mode. The variable frame rate imaging mode is preconfigured with at least two imaging frame rates. The preconfigured imaging frame rates at least include a first imaging frame rate, and each imaging frame rate is preconfigured with corresponding imaging parameters.

In some embodiments of the present disclosure, the instruction to enter the variable frame rate imaging mode may be an operational instruction input by a user through a touchscreen display or an external input device, or a control instruction input by the user through voice input.

In some embodiments, the preconfigured imaging frame rate under the variable frame rate imaging mode at least includes a first imaging frame rate, and in addition to the first imaging frame rate, includes at least one imaging frame rate, all of which are different. Different imaging frame rates can be set according to the requirements of different phases during the imaging process.

Step 402: under the variable frame rate imaging mode: within a period of time after a contrast agent is injected, according to the imaging parameters preconfigured for the first imaging frame rate, emitting ultrasonic waves to the region of interest of the target object and receiving ultrasonic echoes from the target object so as to obtain ultrasonic data with the first imaging frame rate.

In some embodiments, the first imaging frame rate may be equal to the fixed imaging frame rate under the fixed frame rate imaging mode, or may be another preconfigured imaging frame rate.

Step 403: after the contrast agent is injected and a predefined condition is met, according to imaging parameters preconfigured for an imaging frame rate corresponding to the predefined condition, emitting ultrasonic waves to the region of interest of the target object and receiving ultrasonic echoes from the target object so as to obtain ultrasonic data with the corresponding imaging frame rate, wherein each imaging frame rate corresponds to one or more predefined conditions.

In some embodiments, the preset conditions include time periods corresponding respectively to one or more phases during the imaging process of the contrast agent. For example, the preset conditions may include a time period corresponding to an early arterial phase, and may also include time periods corresponding to the arterial phase, the portal phase, and the Kupffer phase. That is, different imaging frame rates may be set according to the time periods corresponding to one or more of the above phases to meet the imaging requirements of different phases. It should be noted that the time phases corresponding to the preset conditions in this embodiment can include all time phases during the imaging process, or only some of them, which can be determined by the user.

In some embodiments, the time period corresponding to each time phase during the imaging process of the contrast agent includes the start time and end time of each corresponding time phase, where the start time is a start time of each corresponding phase, measured from start of the injection of the contrast agent, and the end time is an end time of each corresponding phase, measured from start of the injection of the contrast agent. The start time and end time of each corresponding time phase can be manually set by users or automatically set by the system. Specifically, it may include: in response to the time parameter preconfigured by a user, obtaining the start time and/or end time corresponding to each time phase; or, automatically detecting the start time and/or end time corresponding to each time phase based on the ultrasonic data obtained according to the imaging parameters preconfigured for the first imaging frame rate.

In this embodiment, the specific setting ways to the starting time and the end time corresponding to different phases can refer to the setting ways to the first time and the second time corresponding to the early arterial phase in the above embodiments. In addition, the setting for the first imaging frame rate and the imaging frame rates corresponding to each preset condition can also refer to the setting for the first imaging frame rate and the second imaging frame rate in the above embodiments, where each imaging frame rate can be manually adjusted by users within a certain range during the contrast imaging process.

Step 404: generating a contrast image having at least two imaging frame rates based on the ultrasonic data with the first imaging frame rate and ultrasonic data with at least one preconfigured imaging frame rate other than the first imaging frame rate.

Therefore, according to the above embodiments, different imaging frame rates can be used for contrast imaging at different time phases, thereby meeting the contrast requirements at different time phases.

The specific examples employed above to illustrate the present invention are for the purpose of facilitating understanding and are not intended to limit the invention. Those skilled in the art to which the present invention pertains, without departing from the basic principles of the present invention, may make various simple deductions, modifications or substitutions.

What is claimed is:

1. An ultrasonic contrast imaging method, comprising:

in response to an instruction to enter a variable frame rate imaging mode, entering the variable frame rate imaging mode that is preconfigured at least with a first imaging frame rate and a second imaging frame rate that are each preconfigured with corresponding imaging parameters, with the second imaging frame rate being higher than the first imaging frame rate; and under the variable frame rate imaging mode:

when a contrast agent is injected into a target object, according to the imaging parameters preconfigured for the first imaging frame rate, emitting ultrasonic waves to a region of interest of the target object and receiving ultrasonic echoes from the target object to obtain ultrasonic data with the first imaging frame rate;

after the contrast agent is injected and a first predefined condition is met, according to the imaging parameters preconfigured for the second imaging frame rate, emitting ultrasonic waves to the region of interest of the target object and receiving ultrasonic echoes from the target object to obtain ultrasonic data with the second imaging frame rate; and generating a contrast image based on the ultrasonic data with the first imaging frame rate and the ultrasonic data with the second imaging frame rate, wherein the contrast image has at least the first imaging frame rate and the second imaging frame rate.

2. The method according to claim 1, wherein the first predefined condition comprises: a time period corresponding to an early arterial phase during an imaging process of the contrast agent.

3. The method according to claim 2, wherein the time period corresponding to the early arterial phase includes a first time and a second time, wherein the first time is a start time of the early arterial phase, measured from start of the injection of the contrast agent, and the second time is an end time of the early arterial phase, measured from start of the injection of the contrast agent; and the method further comprises:

obtaining the first time and/or the second time in response to a time parameter preconfigured by a user;

or, automatically detecting the first time and/or the second time based on the ultrasonic data obtained according to the imaging parameters preconfigured for the first imaging frame rate.

4. The method according to claim 3, wherein automatically detecting the first time based on the ultrasonic data obtained according to the imaging parameters preconfigured for the first imaging frame rate, comprises:

within a period of time after the contrast agent is injected, obtaining reference ultrasonic data based on the ultrasonic data obtained according to the imaging parameters preconfigured for the first imaging frame rate within said period of time;

after obtaining the reference ultrasonic data, either obtaining current ultrasonic data once every fixed time interval according to the imaging parameters preconfigured for the first imaging frame rate, and taking each obtained current ultrasonic data as target ultrasonic data or taking each frame of ultrasonic data obtained according to the imaging parameters preconfigured for the first imaging frame rate as target ultrasonic data; and determining a time when an average intensity difference between currently obtained target ultrasonic data and the reference ultrasonic data is greater than or equal to a threshold as the first time.

5. The method according to claim 1, wherein under the variable frame rate imaging mode, the method further comprises:

in response to an instruction to adjust imaging frame rate from a user, adjusting the first imaging frame rate and/or the second imaging frame rate.

6. The method according to claim 1, wherein the first predefined condition is met during a time period from a start time of the early arterial phase to an end time of the early arterial phase.

7. The method according to claim 1, wherein the emitting of the ultrasonic waves to the region of interest of the target object and the receiving of the ultrasonic echoes from the target object to obtain the ultrasonic data with the first imaging frame rate according to the imaging parameters preconfigured for the first imaging frame rate when the contrast agent is injected into the target object comprises:

after the contrast agent is injected into a target object, according to the imaging parameters preconfigured for the first imaging frame rate, emitting ultrasonic waves to the region of interest of the target object and receiving the ultrasonic echoes from the target object to obtain ultrasonic data with the first imaging frame rate, in a time period before the start time of the early arterial phase and a time period after the end time of the early arterial phase.

8. An ultrasonic imaging apparatus, comprising:

a probe;

a transmit circuit configured to excite the probe to emit ultrasonic waves to a target object;

a receive circuit configured to receive ultrasonic echoes from the target object through the probe to obtain ultrasonic echo signals;

a processor configured to process the ultrasonic echo signals to obtain an ultrasonic image of the target object; and a display configured to display the ultrasonic image;

wherein the processor is further configured for:

in response to an instruction to enter a variable frame rate imaging mode, entering the variable frame rate imaging mode that is preconfigured at least with a first imaging frame rate and a second imaging frame rate that are each preconfigured with corresponding imaging parameters, with the second imaging frame rate being greater than the first imaging frame rate; and under the variable frame rate imaging mode:

when a contrast agent is injected into a target object, according to the imaging parameters preconfigured for the first imaging frame rate, emitting ultrasonic waves to a region of interest of the target object and receiving ultrasonic echoes from the target object to obtain ultrasonic data with the first imaging frame rate;

after the contrast agent is injected and a first predefined condition is met, according to the imaging parameters preconfigured for the second imaging frame rate, emitting ultrasonic waves to the region of interest of the target object and receiving ultrasonic echoes from the target object to obtain ultrasonic data with the second imaging frame rate; and generating a contrast image based on the ultrasonic data with the first imaging frame rate and the ultrasonic data with the second imaging frame rate, wherein the contrast image has at least the first imaging frame rate and the second imaging frame rate.

9. The ultrasonic imaging apparatus according to claim 8, wherein the first predefined condition comprises: a time period corresponding to an early arterial phase during an imaging process of the contrast agent.

10. The ultrasonic imaging apparatus according to claim 9, wherein the time period corresponding to an early arterial phase includes a first time and a second time, wherein the first time is a start time of the early arterial phase, measured from start of the injection of the contrast agent, and the second time is an end time of the early arterial phase, measured from start of the injection of the contrast agent; and the processor is further configured for:

obtaining the first time and/or the second time in response to a time parameter preconfigured by a user;

or, automatically detecting the first time and/or the second time based on the ultrasonic data obtained according to the imaging parameters preconfigured for the first imaging frame rate.

11. The ultrasonic imaging apparatus according to claim 10, wherein automatically detecting the first time based on the ultrasonic data obtained according to the imaging parameters preconfigured for the first imaging frame rate comprises:

within a period of time after the contrast agent is injected, obtaining reference ultrasonic data based on the ultrasonic data obtained according to the imaging parameters preconfigured for the first imaging frame rate;

after obtaining the reference ultrasonic data, either obtaining current ultrasonic data once every fixed time interval according to the imaging parameters preconfigured for the first imaging frame rate and taking each obtained current ultrasonic data as target ultrasonic data, or taking each frame of ultrasonic data obtained according to the imaging parameters preconfigured for the first imaging frame rate as target ultrasonic data; and determining a time when an average intensity difference between currently obtained target ultrasonic data and the reference ultrasonic data is greater than or equal to a threshold as the first time.

12. The ultrasonic imaging apparatus according to claim 8, wherein the processor is further configured for:

under the variable frame rate imaging mode, in response to an instruction to adjust imaging frame rate from a user, adjusting the first imaging frame rate and/or the second imaging frame rate.

* * * * *